United States Patent [19]

Kang et al.

[11] 4,269,939

[45] May 26, 1981

[54] PREPARATION OF HETEROPOLYSACCHARIDE S-119

[75] Inventors: Kenneth S. Kang, La Jolla; George T. Veeder; Peter J. Mirrasoul, both of San Diego, all of Calif.

[73] Assignee: Merck & Co., Inc., Rahway, N.J.

[21] Appl. No.: 161,619

[22] Filed: Jun. 20, 1980

[51] Int. Cl.$^3$ ............................................. C12P 19/06
[52] U.S. Cl. .................................................... 435/104
[58] Field of Search .......................................... 435/104

[56] References Cited

PUBLICATIONS

Amemura et al., Journal Fermentation Technology, vol. 49, No. 6 pp. 559–564, 1971.
Hisamatsu et al., Carbohydrate Research vol. 61 pp. 89–96 (1978).
Chemical Abstracts vol. 75: 74882j (1971).

*Primary Examiner*—Lionel M. Shapiro
*Attorney, Agent, or Firm*—Gabriel Lopez; Hesna J. Pfeiffer; Julian S. Levitt

[57] ABSTRACT

A process for producing heteropolysaccharide S-119 by bacterial fermentation of an organism deposited with the American Type Culture Collection under Accession No. ATCC 31643.

4 Claims, No Drawings

PREPARATION OF HETEROPOLYSACCHARIDE S-119

CROSS REFERENCE

This application is related to two other applications filed on even date herewith: Ser. No. 161,618, entitled "Use of Heteropolysaccharide S-119 As An Antimigrant" and Ser. No. 161,625, entitled "Organism ATCC 31643."

BACKGROUND OF THE INVENTION

It is known that heteropolysaccharides can be produced by certain microorganisms. Some of such heteropolysaccharides function as hydrophilic colloids and because of their viscosity properties and rheology have been used as thickening agents for aqueous systems.

Organisms classified as *Agrobacterium radiobacter* IFO (Institute of Fermentation, Osaka) 12607, IFO 12664, IFO 12665, IFO 13127, IFO 13256, IFO 13532 and IFO 13533 have been used to produce exocellular polysaccharides (Hisamatsu, et al., "Acidic Polysaccharides Containing Succinic Acid in Various Strains of Agrobacterium", Carbohydrate Research, 61 (1978) 89–96). These organisms were grown in a synthetic medium described in Amemura, et al., Hakko Kogaku Zasshi; 49 (1971) 559–564, Chem. Abst. 75, 1971, 74882j.

An exopolysaccharide containing D-glucose, D-galactose, pyruvic acid, and O-acetyl groups in the approximate proportions 6:1:1:1.5 is described by L. P. T. M. Zevenhuizen, "Methylation Analysis of Acidic Exopolysaccharides of Rhizobium and Agrobacterium", Carbohydrate Research, 26 (1973) 409–419. The organisms used by Zevenhuizen are described as *A. tumefaciens* A-8 and A-10.

SUMMARY OF THE INVENTION

It has now been found that a variant strain of *A. radiobacter*, ATCC 31643, produces a water-soluble heteropolysaccharide of composition similar to that described for *A. tumefaciens* A-8 and A-10 when incubated in a selected nutrient medium. An unrestricted deposit of this hitherto undescribed organism was made with the American Type Culture Collection on May 12, 1980, under Accession No. ATCC 31643.

DETAILED DESCRIPTION

The organism was isolated from a soil sample obtained in Kahuka, Hawaii. The organism was picked as a gummy colony after five days' incubation at 30° C. from an E-1 agar plate with 1% 42DE corn syrup as the carbon source. The isolate was then pure cultured on nutrient agar.

A YM flask seed was started with a fresh NA plate and placed on a gyrotary shaker at 30° C. Approximately 24 hrs. later this seed was used to inoculate an E-1 flask with 3% hydrolyzed starch as the carbon source. This flask was also placed on a shaker at 30° C. Approximately 72 hrs. later the flask was noted to have viscous beer and upon addition of two volumes of 99% IPA a fibrous precipitate was observed.

Another YM seed flask was prepared in the above fashion and used at 24 hrs. to inoculate four flasks containing various media. These flasks were incubated on a shaker at 30° C. for about 72 hrs. at which the pH, viscosity, gum yield, and product viscosity were measured. The results are shown in Table 1.

TABLE 1

EFFECT OF MEDIA ON GUM PRODUCTION

| Medium | pH | Beer Vis. (cP) | Gum Yield(%) | 1% Product Vis. (cP) |
|---|---|---|---|---|
| E-1 | 7.4 | 120 | 0.650 | ND |
| E-1 − NH$_4$NO$_3$ + 0.19% KNO$_3$ | 8.2 | 160 | 0.310 | ND |
| E-1 + 0.15% Promosoy 100 | 7.2 | 1000 | 1.278 | ND |
| E-1 + HoLe salts | 6.9 | 1800 | 1.524 | 800 |

ND: Not determined

E-1 medium contains 5 gms of dipotassium phosphate, 0.1 gm of magnesium sulfate, 0.9 gm of ammonium nitrate, 0.5 gm of Promosoy 100 (an enzymatic digest of soybean meal sold by Central Soya Chemurgy Division), 30 gms of dextrose and 1 liter of tap water. The pH of the E-1 medium is about 7.6 to 7.8.

The organism has been scaled-up in 14L and 70L fermentors. The data on these scale-ups is given in Table 2. Viscosities are measured on a Brookfield LVF viscometer at 60 rpm, room temperature, with spindle 2 (<500 cP), 3 (500–2000 cP), or 4 (>2000 cP).

TABLE 2

| Medium | Age (hrs) | Beer Vis. (cP) | RCS(%)* | Gum Yield (%) | 1% Product Vis.(cP) |
|---|---|---|---|---|---|
| E-1 + HoLe salts 1 ppm Fe++ | 0 | — | 3.07 | — | — |
|  | 63 | 1430 | 0.1 | 2.03 | 450 |
| Same as above | 0 | — | 2.55 | — | — |
|  | 42 | 1330 | 0.1 | 1.60 | 370 |
| Same as above | 0 | — | 3.05 | — | — |
|  | 38 | 1270 | 0.1 | 1.84 | 355 |
| Same as above + 0.03% Promosoy 100 + 0.01% MgSO$_4$. 7H$_2$O + 0.06% NH$_4$NO$_3$. Total of 5% glucose added as carbon source | 0 | — | ND | — | — |
|  | 38 | 1490 | 0.86 | 1.86 | — |
|  | 77 | 2350 | 0.1 | 2.41 | 440 |

*Residual carbon source; fermentation is "complete" when RCS ≦ 0.1%.

The following is a summary of the taxonomic study of ATCC 31643, hereinafter also referred to as S-119.

A. Characteristics of Colonial Morphology

On nutrient agar, small translucent non-pigmented colonies (0.2–0.3 mm in diameter) appear in 2 days at ambient temperature; diameter reaches 1.2–1.5 mm after 5 days' incubation. The colonies are round, entire, and convex. Slimy properties are not observed.

On YM agar, small opaque, mucoid, white-to-gray colonies (0.2–0.3 mm in diameter) appear in 2 days at ambient temperature; diameter reaches 2.2–2.5 mm after 5 days' incubation. The colonies are round, entire, and convex, but a thick wrinkled formation appears after prolonged incubation. No hard membraneous texture is observed, although it is slimy.

B. Characteristics of Cell Morphology

The strain S-119 is a gram-negative, rod-shaped bacterium. On nutrient agar the average size of the cell is 0.5 by 0.8–1.2 μm, round at both ends. Vacuole-like structures are often observed. Bipolar strain may be common.

On YM agar the cells are larger; average size is about 0.6 by 2.0–2.5 μm, round at both ends. One end is larger than the other. Vacuoles often appear and this causes uneven staining of the cell. Some cells tend to have a curvature, and pallisade arrangement of cells is common. Y-shaped cells are occasionally observed. Motility is by means of the mixed flagellation, polar monotrichously, and peritrichously flagellation.

C. Physiological and Biochemical Characteristics

Cytochrome oxidase, catalase positive; aerobic. Organism is capable of growth at 41° C. but not at 43° C. Survival at 60° C. for 30 minutes. Tolerance to 3.0% but not to 6.5% NaCl. Growth at pH's between 5 and 12.

Many carbohydrates were utilized. Acid but not gas was produced from the following carbohydrates.
D-Xylose
L-Arabinose
D-Glucose
Fructose
Galactose
Mannose
Lactose
Maltose
Melibiose
Sucrose
Trehalose
Raffinose
Adonitol
Sorbitol
Inositol Acid was not produced from the following carbohydrates.
L-Rhamnose
Dulcitol
Salicin
Inulin Neutral or weak alkali reaction observed. No serum zone formed. $H_2S$ produced from cystein. ADH, LDC and ODC were negative. Indole, VP, MR, and Simmon's citrate tests were negative. Gelatin, casein, starch, Tween 80, esculin, and egg yolk were not hydrolyzed. The 3-Ketolactose test was negative.

Organisms grown on EMB, MacConkey, and SS agar but not on Mannitol salt or Tellurite Blood agar. Congo Red dye was absorbed. Tolerance to 0.02 and 0.1% tiphenyltetrazolium chloride.

D. Antibiotic Susceptibility Test

The strain S-119 is susceptible to the following antibiotics.

| Kanamycin | 30 μg | Erythromycin | 15 μg |
| --- | --- | --- | --- |
| Neomycin | 30 μg | Tetracycline | 30 μg |
| Chlortetracycline | 5 μg | Gentamicin | 10 μg |
| Novobiocin | 30 μg | Carbenicillin | 50 μg |

The strain S-119 is not susceptible to the following antibiotics.

| Penicillin | 10 units | Colistin | 10 μg |
| --- | --- | --- | --- |
| Streptomycin | 10 μg | Polymyxin B | 300 units |

E. Nutritional Characteristics

Growth factors are not required for growth. Ammonium salts serve as sole nitrogen source. At least 53 out of the 114 organic compounds tested are utilized as a sole source of carbon and energy. They are as follows:

D-Ribose
D-Xylose
D-Arabinose
L-Arabinose
D-Fucose
L-Rhamnose
D-Glucose
D-Mannose
D-Galactose
D-Fructose
Sucrose
Trehalose
Maltose
Cellobiose
Lactose
Gluconate
2-Ketogluconate
Salicin
Acetate
Propionate
Succinate
Fumarate
D-Malate
DL-Lactate
DL-Glycerate
Citrate
Pyruvate
Mannitol
Sorbol
Adonitol
Glycerol
Ethanol
N-Propanol
p-Hydroxybenzoate
Quinate
Glycine
L-α-Alanine
D-α-Alanine
β-Alanine
L-Serine
L-Threonine
L-Leucine
DL-Norleucine
L-Aspartate
L-Glutarate
DL-Arginine
DL-Ornithine
α-Aminobutyrate
L-Histidine
L-Proline
L-Tyrosine
Betaine
Sarcosine

F. Biochemical and Other Miscellaneous Tests

See Table 3.

G. Identification

The strain S-119 is a gram-negative, aerobic, rod-shaped organism. Motile by mixed (i.e., polar and peritrichous) flagella. Oxidase and catalase are positive. Many carbohydrates are utilized. Cells are often pear-shaped; vacuolated forms in pallisade arrangement of cells are common. Y-shaped forms and accumulation of poly-β-hydroxybutyrate may be observed. Citrate is utilized. According to the Bergey's Manual (8th edition) the organism is a member of the genus Agrobacterium. The similarity value ($S_j$) of the organism compared with a reference strain *Agrobacterium radiobacter* (ATCC 19358) showed 76.9%, which is within the species level according to Colwell and Liston (1961). This organism does not produce 3-ketolactose. Therefore this organism is a variant strain of *Agrobacterium radiobacter*.

TABLE 3
Biochemical and Other Miscellaneous Tests Employed for the Strain S-119

| | | | |
|---|---|---|---|
| Oxidase - Kovac's | + | Hydrolysis of: | |
| Pathotech | + | Gelatin | − |
| Catalase | + | Casein | − |
| OF medium: oxidative | + | Starch | − |
| fermentative | − | Tween 80 | − |
| Gas from glucose | − | Pectin | − |
| $H_2S$ production: T & I | − | Alginate | − |
| Cystine | + | Cellulose | − |
| Ammonium from peptone | NT | Chitin | − |
| β-Galactosidase | ± | DNA | NT |
| Arginine dihydrolase | − | Esculin | − |
| Lysine decarboxylase | − | Growth on various media: | |
| Ornithine decarboxylase | − | EMB agar | + |
| Tryptophan deaminase | NT | MacConkey agar | + |
| Phenylalanine deaminase | NT | SS agar | + |
| Urease | − | Mannitol salt agar | − |
| Indole | − | TCBS agar | − |
| MR test | − | Tinsdale tellurite | |
| VP test | − | blood agar | − |
| Nitrate reduction | − | Pseudosel agar | − |
| Nitrate reduction | − | Pigment production: | |
| Denitritication | NT | King A medium | − |
| N-fixation: | | King B medium | − |
| Growth on Burk's medium | − | Dye Reaction: | |
| Nitrogenase activity | NT | Congo Red | + |
| Malonate (oxidation) | − | Nile Blue | NT |
| Phosphatase | − | | |
| Haemolysis | − | | |
| Litmus milk: | | | |
| Change in color | None | | |
| peptonization | None | | |
| reduction | None | | |
| 3-Ketolactose | − | | |
| Survival at 60° C. for 30 min. | + | | |
| T & I: Slant | No change | | |
| Butt | No growth | | |
| Gas | − | | |
| Egg Yolk Reaction | − | | |

NT = Not Tested

FERMENTATION CONDITIONS

Heteropolysaccharide S-119 is produced during the aerobic fermentation of suitable aqueous nutrient media under controlled conditions via the inoculation with the organism ATCC 31643. The media are usual media, containing source of carbon, nitrogen and inorganic salts.

In general, carbohydrates (for example, glucose, fructose, maltose, sucrose, xylose, mannitol and the like) can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 2% and 5% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrosylates, primary yeast, soybean meal, cottonseed flour, hydrolysates of casein, corn-steep liquor, distiller's solubles or tomato paste and the like. The sources of nitrogen, either alone or in combination, are used in amounts preferably ranging from about 0.05% to 0.2% by weight of the aqueous medium. Promosoy 100 has been used in the range 0.005 to 0.4%.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the examples are merely illustrative of the wide variety of media which may be employed, and are not intended to be limiting.

As an alternate medium, S-119 may be grown under low $Ca^{++}$ conditions, i.e., in deionized water or some other aqueous system substantially free of $Ca^{++}$ ions (i.e., less than about 4 ppm $Ca^{++}$ per 1% gum in the final fermentor broth).

The fermentation is carried out at temperatures ranging from about 25° C. to 35° C.; however, for optimum results it is preferable to conduct the fermentation at temperatures of from about 28° C. to 32° C. The pH of the nutrient media for growing the ATCC 31643 culture and producing the polysaccharide S-119 can vary from about 6 to 8.

Although the polysaccharide S-119 is produced by both surface and submerged culture, it is preferred to carry out the fermentation in the submerged state.

A small scale fermentation is conveniently carried out by inoculating a suitable nutrient medium with the culture and, after transfer to a production medium, permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1–2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. the inoculated flasks are shaken at a constant temperature for several days, and at the end of the incubation period the contents of the flasks are recovered by precipitation with a suitable alcohol such as isopropanol, conveniently in the form of CBM (an 85:15 alcohol:water constant boiling mixture).

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-119 is particularly suited for the preparation of large quantities.

Although ATCC 31643 can be grown under a broad spectrum of media conditions, the following preferred conditions are recommended.

1. Culture Maintenance

The culture grows quite well on nutrient agar (NA) or YM agar, but NA is preferred for culture maintenance.

2. Seed Preparation

Seed preparation for this organism is started in YM broth incubated at 30° C. The YM seeds are then used at 24–30 hrs to inoculate seed medium. The composition of the seed medium is as follows:

3.0%—Glucose
0.5%—$K_2HPO_4$
0.05%—Promosoy 100
0.09%—$NH_4NO_3$
0.01%—$MgSO_4.7H_2O$
1 ppm—Fe++
1 ppm—Mn++

A 5 to 10% inoculum size is used at 24–30 hrs to inoculate the final fermentor.

3. 70L Fermentor Medium 5.0%—Glucose
0.05%—$K_2HPO_4$
0.20%—Promosoy 100
0.15%—$NH_4NO_3$
0.05%—$MgSO_4.7H_2O$
1 ppm—Fe++
1 ppm—Mn++

The pH should be controlled at 6.5–7.2; the temperature at 30° C.

Fermentation times range from 60–70 hrs with beer viscosity ranging from 1900 cP to 2300 cP. Conversion efficiencies vary from 48–52% with 5% glucose. Antifoam SAG 471 (Union Carbide) is used.

Gram stains made from S-119 fermentation beer show gram-negative club-shaped cells approximately 0.6×2.02.5μ in size.

4. Recovery

On completion of the fermentation, the heteropolysaccharide S-119 may be recovered by treatment of the fermentation beer with a miscible solvent which is a poor solvent for the heteropolysaccharide and does not react with it. In this way the heteropolysaccharide is precipitated from solution. The quantity of solvent employed generally ranges from about 2 to about 3 volumes per volume of fermentation beer. Among the various solvents which may be employed are acetone and lower alkanols such as methanol, ethanol, isopropanol, n-butanol, sec-butanol, tertiary butanol, isobutanol, and n-amyl alcohol. Isopropanol is preferred. Precipitation of S-119 is facilitated when the fermentation beer is first heated to a temperature of about 70° to 75° C. for a short time, e.g., about 5 to 10 minutes, and then cooled to about 30° C. or lower before addition of the solvent. A spent alcohol concentration of 57–59% is required for precipitation. Thus, this is a preferred method of precipitating the heteropolysaccharide from the fermentation beer. The solid is recovered by separating it from the liquid, as by filtering or straining, and then drying at elevated temperature.

5. Drying

The product is dried at 55° C. for up to one hour in a forced-air tray drier.

6. Product Quality

One percent deionized water viscosities range from 250–450 cP as measured on a Brookfield LVF, spindle 2, 60 rpm at 25° C.

HETEROPOLYSACCHARIDE S-119

The heteropolysaccharide produced by ATCC 31643 is composed of principally carbohydrate, 2.9–3.5% (calculated as O-acetyl) O-acyl groups as the O-glycosidically linked esters, which are acetyl or succinyl or a combination thereof, 3.0–4.0% pyruvate, and about 12% protein. It has a negative optical rotation, indicating principally β-linkages ($[\alpha]_{589} = -14°$; $[\alpha]_{578} = -15°$). These values were obtained from 1% solutions in D.I. water.

The carbohydrate portion of the S-119 polysaccharide contains no uronic acid and the neutral sugars glucose (88%) and galactose (12%). The approximate molar ratio of glucose to galactose is 7.4:1. Colloidal titration (DIMDAC/sulphonic acid method) indicates the gum is anionic (0.9 m. equivalents of anionic groups/g. gum).

The acetyl content of 3.5% was determined by treating a 0.2% aqueous solution of S-119 gum with an alkaline, hydroxylamine reagent followed by treatment with an acidic ferric chloride reagent [S. Hestrin (1949) *J. Biol. Chem.* 180 249–261].

The neutral sugars of polysaccharide S-119 were determined by dissolving ten mg. of the product in 2 ml 2 N $H_2SO_4$, and the mixture is heated at 100° C. for 4 hours. The resulting solution is cooled, neutralized with barium hydroxide and the pH is brought to 5–6 with solid carbon dioxide. The resulting precipitate of barium sulfate is removed by centrifugation and the supernatent is concentrated to a syrup under reduced pressure. The sugars in the hydrolysate are tentatively identified by gas-liquid chromatography of their aldononitrile acetone derivatives on a Hewlett-Packard Model 5750 chromatograph using 3% by weight OV-225 on 80/100 mesh Gas Chrom Q at 210° C. The sugars are identified and quantitated by comparison with authentic standards [J. K. Baird, M. J. Holroyde, and D. C. Ellwood (1973) Carbohydr. Res. 27 464–467].

The various neutral sugars of the polysaccharides were also characterized by use of descending paper chromagraphy on Whatman No. 1 chromatography paper using as the solvent the upper layer of pyridine: ethyl acetate:water (2:5:5). Chromatograms were stained using silver nitrate dip and acid aniline phthalate spray reagent. Component sugars were identified by co-chromatography with sugar standards and by the specific-color reaction with the analine phthalate reagent.

The uronic acid content of the polysaccharide was determined by two separate methods. In one method the sample was decarboxylated with 19% hydrochloric acid and the liberated carbon dioxide was trapped in standard sodium hydroxide and determined by back titration [B. L. Browning (1967) *Methods of Wood Chemistry II*, 632–633] and by the carbazole colorimetric method [T. Bitter and H. M. Muir (1962) *Anal. Biochem.* 4, 330–334]. The decarboxylation method gave the value 2.8%; colorimetric gave 4.8%.

Paper electrophoresis was used for the separation and tentative identification of the uronic acids present in the neutralized acid hydrolysate described above. Aliquots of this and known uronic acid standards were applied to Camag electrophoresis paper No. 68-011 and electrophoresis was carried out for 2.0 hours in a pH 2.7 buffer using a Camag Model HVE electrophoresis apparatus. Chromatograms were air dried and stained with silver nitrate dip reagent to locate the uronic acids being separated. No uronic acid spots were found by this method.

An infrared spectrum of native S-119 was made on dried material in a KBr pellet. The heteropolysaccharide evidenced peaks at: 1725 cm$^{-1}$, 1600–1650 cm$^{-1}$, and 1350–1400 cm$^{-1}$.

Heteropolysaccharide S-119 has the following profile of properties (all measurements are at room temperature):

1. VISCOSITY (Brookfield LVT Viscometer)

| Conc. | Spindle | RPM | D.I. H$_2$O | Viscosity (cP) D.I. + 0.1% KCl |
|---|---|---|---|---|
| 1.0% | 3 | 60 | 920 | 1050 |
| — | 3 | 6 | 6900 | — |
| 0.1% | 1 + UL adap. | 6 | 35 | 30 |
| 0.5% | (Wells-Brookfield @ 9.6 sec$^{-1}$) | — | 440 | 490 |

2. SHEAR (Wells-Brookfield Microviscometer RVT - c/P)

1. n @ 1.92 sec$^{-1}$ 5120 cP    4. n @ 384 sec$^{-1}$ 30 cP
2. n @ 9.6 sec$^{-1}$ 1270 cP    5. n @ 384 sec$^{-1}$ 40 cP
3. n @ 76.8 sec$^{-1}$ 210 cP    6. n @ 96 sec$^{-1}$ 1240 cP

3. 50° C. STORAGE STABILITY (4 weeks)

Day 1: 447.5 cP, Brookfield LVT, spindle No. 2, 60 rpm.
Week 4: 540 cP, Brookfield LVT, spindle No. 3, 60 rpm.

4. ACID, BASE, HEAT, STABILITY

A. Stability

| | Initial n | Final n | % Change |
|---|---|---|---|
| 1. Acetic acid plus heat | 1170 cP | 970 cP | −17 |
| 2. 1% HCl plus heat | 1330 cP | Total loss | Total loss |
| 3. 1% NaOH plus heat | 970 cP | 270 cP | −72 |
| 4. Heat only | 1230 cP | 500 cP | −59 |

B. pH Effect (Wells-Brookfield RVT - c/P @ 9.6 sec$^{-1}$)

| | | |
|---|---|---|
| 1. 5% Acetic acid | 2.98 pH | 1050 cP |
| 2. 5% NH$_4$OH | 10.83 pH | 1370 cP |

5. SALT & DYE COMPATIBILITY

A. Salt

| | |
|---|---|
| 1. CaCl$_2$ (Saturated) | Compatible |
| 2. Amm. polyphosphate | Precipitate |
| 3. 60% NH$_4$NO$_3$ | Compatible |
| 4. 1% Al$_2$(SO$_4$)$_3$ · 18H$_2$O | Compatible |
| 5. 1% CaCl$_2$ · 2H$_2$O | Compatible |
| 6. 1% KCl | Compatible |
| 7. 0.1% KCl | 1570 cP* |
| 8. 2.5% KCl | 1580 cP |

B. Dyes

| | |
|---|---|
| 1. Milling Green | Compatible |
| 2. Methylene Blue | Precipitate |

6. TEXTURE/FLOW PROPERTIES

High viscosity gum, smooth continuous flow, elastic, no gelation, slightly gummy to the touch.

7. SYNERGISM & ENZYMES
(Wells-Brookfield RVT - c/P at 9.6 sec$^{-1}$)

| | 1% n | 0 hour n of mixture | 2 hour n of mixture | Expected viscosity | Synergism |
|---|---|---|---|---|---|
| A. Guar | 1290 cP | 850 cP | 1340 cP | 1250 cP | +7% |
| B. H.P. Guar | 1820 cP | 1410 cP | 1430 cP | 1500 cP | None % |
| C. CMC | 790 cP | 450 cP | 490 cP | 980 cP | None % |
| D. HEC | 590 cP | 870 cP | 910 cP | 850 cP | +7% |
| E. S-119 | 1230 cP | | | | |

8. MILK REACTIVITY

A. Dispersion: Excellent
B. Whey off: 1st day

9. FILM FORMATION

Film formed, slightly plastic, high tensile strength.

*(Wells-Brookfield RVT - c/P @ 9.6 sec$^{-1}$)

Heteropolysaccharide S-119 can be used in aqueous compositions, for example, as an antimigrant in pad-dyeing systems.

In commercial dyeing operations in which a substrate is impregnated by padding with an aqueous dye-bath liquid, as in the conventional Thermosol process (a well-established procedure for commercial dyeing operations), the dye-impregnated substrate is commonly subjected to an intermediate drying stage prior to thermofixation or reduction of the dye. It is during this intermediate drying stage that problems with migration of the dye can occur. Migration of the dye is undesirable as the substrate becomes mottled, or unevenly shaded, thereby detracting from the appearance and the value of the dyed textile substrate.

In the conventional drying operation following the impregnating of the textile with the desired dye, the treated substrate is heated and held for a time sufficient to dry off the dye-bath liquor, conveniently at a temperature of about 100° C. for convenience of rapid action by any suitable means such as hot air, infrared radiation, microwave oven, or the like. Pressures may range from below to above atmospheric pressure. It is during this convention drying operation that dye migration to the substrate surface is known to occur, said migration tending to be uncontrolled, random, and uneven, resulting in an uneven overall dyeing action, variegation, and a generally inferior quality of the finished product.

Dye migration occurs three-dimensionally; that is, in the warp and filling directions and through the fabric thickness. Migration in the warp direction does not significantly affect substrate appearance; however, migration in the filling direction and through the substrate thickness always will occur to some degree even under proper commercial drying conditions.

As used herein, substrate means a textile such as a woven, non-woven, or knitted fabric, and also yarns, threads, and fibers which can be paid dyed on a continuous basis.

Heteropolysaccharide S-119 may be used in pad-dyeing operations with available dyes and combinations thereof: e.g., disperse, direct, vat, reactive, or acid dyes. Dye/S-119 antimigrant solutions may be used to print any substrate suitable for pad dyeing; for example, 100% polyester, 100% cotton, polyester/cotton blends in any ratio, corduroy, 100% nylon, 100% polypropylene, 100% acrylic, and polyester/cotton/nylon/polypropylene/acrylic blends in any combination and ratio. The use level of S-119 as an antimigrant will vary from 0.001% to over 1.00% based on the total weight of the dye-bath liquor with the S-119 concentration being preferably in the range of about 0.005% to 0.5% by weight. These levels will depend on the type of substrate and dye used as well as the method of application and drying procedure. At S-119 concentrations above 10%, the viscosity of the solution becomes a problem and such solutions are not recommended. However, 50% aqueous pastes can be made up and 30% solutions are pourable so concentrates can be prepared for later dilution.

It should be noted that the pH of the aqueous dye-bath liquor of the invention can generally vary over a rather broad range although it will be appreciated that optimum pH limits will pertain to particular dye-bath systems.

After the textile material being treated has been impregnated with a desired dye by contact with the aqueous dye-bath liquor of the present invention, and the material has been dried by conventional means, the dye is fixed by heat or other means, e.g., by chemical action. Such fixation techniques are well known and established in the textile dyeing art. Illustratively, curing may be carried out at temperatures of about 120° to 230° C. for about three minutes to 15 seconds, depending on the fabric, the dye, and other contributing factors.

It will be appreciated by those skilled in the art that a variety of additives may be present in the aqueous dye-bath liquor apart from the dye itself and the water with which it is associated in the dye-bath liquor. Such additives include dye assistants, carriers, promoters, and the like, and these may be employed in conventional amounts for their usual purposes in the practice of the present invention. The dye itself may be incorporated in the dye-bath liquor in amounts generally up to about 5% or more by weight based on the total weight of the dye bath. For heavier or darker shades the dye may be employed in amounts typically of from about 2% to about 5% by weight, most typically about 3–4% by weight; whereas light shades may be achieved by employing dye concentrations of about ½% by weight or less. Dye concentrations outside such ranges also can be employed within the scope of the invention; however, it is also understood that the amount of said dye-bath liquor with which the textile material is impregnated by padding, spraying, coating, printing, or other means commonly at 25–150% wet pickup will depend upon the color requirements of any given application.

The extent of dye migration can be non-subjectively measured by a test recently adopted by the American Association of Textile Chemists and Colorists (AATCC), as described in "Evaluation of Dyestuff Migration", AATCC Test Method 140-1974, and in *AATCC Technical Manual* (23). Warp- and filling-direction migration can be determined by this test, as can migration through the substrate thickness, by mathematical equations relating the measured horizontal-migration values with the vertical thickness migration.

Briefly, in the AATCC test, a substrate is padded through a dye- and auxiliary-containing bath, is padded to a specified pick-up level, and finally is placed on a flat, non-porous surface (e.g. glass plate) and covered with a watch glass. The watch glass serves to minimize any evaporation and, thus, aids assessment of any particulate migration in the liquid phase by forcing the migration to occur horizontally through the substrate interior, i.e., from the watch-glass covered area to the uncovered area.

The invention is further defined by reference to the following examples, which are intended to be illustrative and not limiting.

EXAMPLE 1

PILOT PLANT PRODUCTION OF HETEROPOLYSACCHARIDE S-119

Seed preparation is started in YM broth incubated at 30° C. The YM seeds are used at 24 hours to inoculate 100 gal. of seed medium which is composed of:
3.0% Glucose
0.5% $K_2HPO_4$
0.05% Promosoy 100
0.09% $NH_4NO_3$
0.01% $MgSO_4.7H_2O$
0.13% Defoamer FCA-200*
+1 ppm $Fe^{++}$
+1 ppm $Mn^{++}$
*Union Carbide At 29 hours, 100 gal. of this medium is used to inoculate the final fermentor.

| Inoculum: | Age - 29 hrs | |
|---|---|---|
| (100 gals) | pH - NA | |
| | Viscosity - 700 cP | |
| Medium: | Glucose | 5.0% |

| | -continued | |
|---|---|---|
| (1100 gals) | $NH_4NO_3$ | 0.15% |
| | $K_2HPO_4$ | 0.05% |
| | Promosoy 100 | 0.20% |
| | $MgSO_4.7H_2O$ | 0.05% |
| | FCA-200 | 0.08% |
| | KOH | To control pH at 6.5–7.2. |
| Fermentation: | | |
| | Time - 63 hrs | |
| | Beer pH - 7.6 | |
| | Temperature - 30° C. | |
| | Aeration - 0 hrs: 40 CFM; | |
| | 15 hrs: 80 CFM; | |
| | 35 hrs: 100 CFM; | |
| | Viscosity - 1680 cP | |
| Agitation: | Disc and turbine impellors | |
| | Number of sets: 3 | |
| | Number of blades/set: 5 | |
| | Disc diameter: 20 inches | |
| | Blade dimension: 2¼" × 4" | |
| | Impellor diameter: 28" | |
| | Speed 150 rpm | |
| Recovery: | Beer pH adjust to 6.9 with $H_2SO_4$ | |
| | Beer rate - 5 gpm | |
| | Pasteurization - 165° F./6–7 min. | |
| | Ppt. with 60% spent IPA | |
| | Dried at 150° F., for ~30 min., max. | |
| | Milled through 40 mesh | |
| | Yield: 2.08% | |

EXAMPLE 2

USE OF S-119 AS AN ANTIMIGRANT

A solution containing 0.5 g/l heteropolysaccharide S-119 and 100 g/l Palacet Black Z-PAT 50% liquid (disperse dye) is padded onto a 100% polyester fabric at a pick up of 80% (based on the weight of the fabric). The fabric is dried and processed in the normal manner. The resulting dyed fabric is uniform in color and free of mottling.

To achieve the same results, 2.0 g/l of algin (KEL-GIN XL ®, Kelco Division, MERCK & CO., Inc.), a known antimigrant is required.

EXAMPLE 3

USE OF S-119 AS AN ANTIMIGRANT

A 60% polyester/40% cotton fabric is padded to a pick up of 80% with a dye bath containing: 1.0 g/l S-119, 3.0 g/l C.I. disperse blue 120 and 2.0 g/l C.I. Direct Blue 98. The padded fabric is dried and processed in the normal manner. The resulting dyed fabric is uniform in color.

Similar results are not obtained when using Superclear 100-N (Diamond Shamrock Corp.) in an amount up to 4.0 g/l (on an active basis).

Similar results are not obtained when using Superclear 100-N (Diamond Shamrock Corp.) in an amount up to 4.0 g/l (on an active basis).

What is claimed is:

1. A process for producing heteropolysaccharide S-119 which comprises growing a variant strain of Agrobacterium radiobacter, ATCC 31643 in an aqueous nutrient medium by aerobic fermentation of an assimilable carbon source and recovering said heteropolysaccharide S-119.

2. A process of claim 1 wherein the assimilable carbon source is 3%–5% glucose.

3. A process of claim 2 wherein the nutrient medium comprises 5.0% glucose, 0.05% $K_2HPO_4$, 0.20% enzymatic digest of soybean meal, 0.15% $NH_4NO_3$, 0.05% $MgSO_4.7H_2O$, 1 ppm $Fe^{++}$, and 1 ppm $Mn^{++}$, the pH ranges from 6.5 to 7.2, and the temperature of the medium is 30° C.

4. A process of claim 2 wherein the nutrient medium is substantially free of $Ca^{++}$.

* * * * *